United States Patent
Steffen et al.

(10) Patent No.: US 10,413,159 B2
(45) Date of Patent: Sep. 17, 2019

(54) VISUALIZATION SYSTEM FOR PROVIDING ENDOSCOPIC IMAGES AND METHOD FOR OPERATION THE SAME

(71) Applicant: Carl Zeiss Meditec AG, Jena (DE)

(72) Inventors: Joachim Steffen, Westhausen (DE); Gerald Panitz, Ellwangen (DE); Christoph Hauger, Aalen (DE); Roland Guckler, Ulm (DE); Konstantinos Filippatos, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 255 days.

(21) Appl. No.: 15/043,385

(22) Filed: Feb. 12, 2016

(65) Prior Publication Data
US 2016/0235276 A1 Aug. 18, 2016

(30) Foreign Application Priority Data
Feb. 12, 2015 (DE) .................. 10 2015 202 605

(51) Int. Cl.
*A61B 1/00* (2006.01)
*A61B 1/04* (2006.01)
(Continued)

(52) U.S. Cl.
CPC .......... *A61B 1/00011* (2013.01); *A61B 1/043* (2013.01); *A61B 90/20* (2016.02);
(Continued)

(58) Field of Classification Search
CPC .. A61B 1/04; A61B 1/043; A61B 1/06; A61B 1/0638; A61B 1/00149;
(Continued)

(56) References Cited

U.S. PATENT DOCUMENTS 5,120,953 A * 6/1992 Harris .................... G02B 21/18
250/216
6,081,371 A * 6/2000 Shioda ............... G02B 21/0012
359/369
(Continued)

FOREIGN PATENT DOCUMENTS

DE          10147806 A1   7/2003
DE     102013215734 A1   2/2015
(Continued)

OTHER PUBLICATIONS

Walter Stummer et al: Technical Principles for Protoporphyrin-IX-Fluorescence Guided Microsurgical Resection of Malignant Glioma Tissue, Acta Neurochirurgica 140: pp. 995 to 1000 (1998), Springer-Verlag, Vienna, Austria.
(Continued)

*Primary Examiner* — Timothy J Neal
*Assistant Examiner* — William B Chou
(74) *Attorney, Agent, or Firm* — Walter Ottesen, P.A.

(57) ABSTRACT

A visualization system includes a surgical microscope assembly for viewing a surgical region under magnification. The surgical microscope assembly is provided with a computer unit having a display for displaying image data. A detection arrangement is configured to detect endoscopic images in the surgical region and is operatively coupled to the surgical microscope assembly. A circuit actuable by a viewing person is configured to detect actuation data. The circuit is configured to set an operating state of the surgical microscope assembly matched to the detection arrangement in response to a presence of the actuation data for the surgical microscope assembly.

11 Claims, 7 Drawing Sheets

(51) Int. Cl.
  *G02B 21/00* (2006.01)
  *A61B 90/20* (2016.01)
  *A61B 90/30* (2016.01)
  *G02B 21/16* (2006.01)
  *G02B 21/36* (2006.01)
  *A61B 90/00* (2016.01)
  *G02B 21/22* (2006.01)
  *A61B 34/20* (2016.01)

(52) U.S. Cl.
  CPC ......... *G02B 21/0012* (2013.01); *G02B 21/16* (2013.01); *G02B 21/361* (2013.01); *A61B 1/00039* (2013.01); *A61B 1/00045* (2013.01); *A61B 2034/2048* (2016.02); *A61B 2090/309* (2016.02); *G02B 21/22* (2013.01)

(58) Field of Classification Search
  CPC ... A61B 5/0059; A61B 5/0071; A61B 5/0082; A61B 5/0084; A61B 90/20; A61B 90/25; G02B 21/0028; G02B 21/365
  USPC ........ 600/102, 103, 109, 113, 117, 118, 178, 600/180, 181, 182
  See application file for complete search history.

(56) References Cited

U.S. PATENT DOCUMENTS

| | | |
|---|---|---|
| 6,398,721 B1 | 6/2002 | Nakamura et al. |
| 6,471,637 B1 | 10/2002 | Chatenever et al. |
| 7,410,462 B2 | 8/2008 | Navok et al. |
| 7,852,371 B2 | 12/2010 | Konstorum et al. |
| 8,659,651 B2 | 2/2014 | Jess et al. |
| 2001/0055062 A1 | 12/2001 | Shioda et al. |
| 2002/0151784 A1 | 10/2002 | Mizoguchi et al. |
| 2003/0069471 A1 | 4/2003 | Nakanishi et al. |
| 2004/0070822 A1 | 4/2004 | Shioda et al. |
| 2005/0020876 A1 | 1/2005 | Shioda et al. |
| 2005/0228229 A1* | 10/2005 | Harris ............... G02B 21/0028 600/168 |
| 2006/0108509 A1 | 5/2006 | Frangioni et al. |
| 2006/0241499 A1 | 10/2006 | Irion et al. |
| 2010/0128221 A1* | 5/2010 | Muller ............... G02B 21/0028 351/207 |
| 2010/0296178 A1* | 11/2010 | Genet ............... A61B 1/00188 359/754 |
| 2010/0321772 A1 | 12/2010 | Reimer et al. |
| 2011/0082334 A1 | 4/2011 | Dolt et al. |
| 2011/0166420 A1* | 7/2011 | Miesner ............. A61B 1/00041 600/160 |
| 2011/0280810 A1* | 11/2011 | Hauger ................ A61B 1/043 424/9.6 |
| 2012/0330157 A1* | 12/2012 | Mandella ........... G02B 21/0028 600/443 |
| 2014/0012078 A1 | 1/2014 | Coussa |
| 2014/0051923 A1 | 2/2014 | Mirza et al. |
| 2015/0198797 A1* | 7/2015 | Andre ................. A61B 5/7425 348/80 |

FOREIGN PATENT DOCUMENTS

| | | |
|---|---|---|
| EP | 2664271 A1 | 11/2013 |
| JP | 2004065317 A | 3/2004 |
| JP | 2011167344 A | 9/2011 |
| NO | 2010114843 A1 | 10/2010 |

OTHER PUBLICATIONS

Andre Ehrhardt et al: Medizin—den Krebs zum Leuchten bringen, Laser+Photonik Mar. 2002, pp. 30 to 32, Carl Hanser Verlag, Munich, Germany.

Andre Ehrhardt et al: Fluorescence Detection of Human Malignancies Using Incoherent Light Systems, Medical Laser Application 18, pp. 27 to 35 (2003), Urban & Fischer Verlag.

Giovanni Profeta et al: Endoscope-assisted microneurosurgery for anterior circulation aneurysms using the angle-type rigid endoscope over a 3-year period, Childs Nerv Syst. 20, pp. 811 to 815 (2004), Springer-Verlag.

"Instruction Manual Photodynamic Diagnostic D-Light C (PDD) System" (2004), pp. 1 to 18, Karl Storz-Endoskope.

"Gebrauchsanweisung D-Light C Modell 20 1336 20" (2004), 44 pages, Karl Storz-Endoskope.

"Gebrauchsanweisung 20 0935 01-1 Karl Storz-SCB System" (2006), 233 pages, Karl Storz-Endoskope.

"Gebrauchsanweisung 20 2230 20-1 Tricam SL II" (2006), 111 pages, Karl Storz-Endoskope.

'Gebrauchsanweisung 20 1336 20-1xx D-Light C1 AP' (2008), 59 pages, Karl Storz-Endoskope.

"Leica FL400—Invisible Becomes Visible" (2010), 8 pages, Leica Microsystems.

Yoshihisa Nishiyama et al: Endoscopic indocyanine green video angiography in aneurysm surgery: an innovative method for intraoperative assessment of blood flow in vasculature hidden from microscopic view, Journal of Neurosurgery 117, pp. 302 to 308 (2012).

Michael Bruneau et al: Endoscope-integrated ICG technology—first application during intracranial aneurysm surgery, Neurosurgical Review 36, pp. 77 to 85 (2012), Springer.

Jan Frederick Cornelius et al: 5-Aminolevulinic Acid and 18F-FET-PET as Metabolic Imaging Tools for Surgery of a Recurrent Skull Base Meningioma, Journal of Neurological Surgery B 74, pp. 211 to 216 (2013), Georg Thieme Verlag KG.

Dorothee Mielke et al: Comparison of Intraoperative Microscopic and Endoscopic ICG Angiography in Aneurysm Surgery, Neurosurgery vol. 10, No. 3, pp. 418 to 425 (2014), Congress of Neurological Surgeons.

Hideyuki Yoshioka et al: The Roles of Endoscope in Aneurysmal Surgery, Neural Med Chir (Tokyo) 55, pp. 469 to 478 (2015).

* cited by examiner

VISUALIZATION SYSTEM FOR PROVIDING ENDOSCOPIC IMAGES AND METHOD FOR OPERATION THE SAME

CROSS REFERENCE TO RELATED APPLICATION

This application claims priority of German patent application no. 10 2015 202 605.1, filed Feb. 12, 2015, the entire content of which is incorporated herein by reference.

FIELD OF THE INVENTION

The invention relates to a visualization system with a surgical microscope for observing a surgical region with magnification, containing a computer unit with a display for displaying image data, and with a device for acquiring endoscopic image data in the surgical region, which is operably coupled to the surgical microscope for displaying the endoscopic image data. Moreover, the invention relates to a method for operating a visualization system with a surgical microscope and with a device for acquiring endoscopic images.

BACKGROUND OF THE INVENTION

U.S. Pat. No. 6,398,721 B1 has disclosed such a visualization system. Described therein is a surgical microscope which has a microscope unit which is held on a stand and which contains optical assemblies for observing a surgical region under magnification with an optical observation beam path. The visualization system has an endoscopic examination device, which may be embodied as a video endoscope, which can be connected to the surgical microscope by way of electrical contacts formed in the microscope unit.

United States patent application publication 2005/0020876 A1 discloses a visualization system with a surgical microscope which has a microscope unit, in which endoscopic image data can be displayed. For the purposes of acquiring the endoscopic image data, there is an endoscope received at a stand device in this visualization system. The position of the endoscope relative to the microscope can be referenced at the stand. This enables visualization of endoscope images in the observation image of the operating system with the correct location and position.

SUMMARY OF THE INVENTION

It is an object of the invention to provide a visualization system and a method for operating a surgical visualization system wherein a display of endoscopic images to a viewing person is made possible in an ergonomically advantageous manner during a surgical procedure.

In the present case, a surgical microscope is understood to mean a system with a microscope unit, preferably embodied as a stereo microscope, which is received at a stand and which enables an observing person to observe a surgical region with magnification. The microscope unit can be configured for visualizing the surgical region with an optical observation beam path. However, it is also possible to provide a microscope unit which brings digitally acquired images to the display for an observing person. An example of a surgical microscope within the meaning of the invention is the OPMI® Pentero® system, manufactured and distributed by Carl Zeiss Meditec AG.

An endoscope within the meaning of the invention is an optical instrument for observing and examining body cavities. Endoscopes within the meaning of the invention have an endoscope body preferably extended in a longitudinal direction. The invention understands a video endoscope to be an endoscope which enables the digital visualization of body cavities. Video endoscopes contain a device for imaging a surgical region on an image sensor. Within the meaning of this invention, endoscopic image data are image data acquired by way of a video endoscope.

The invention proposes that the visualization system contains a circuit which is configured for acquiring actuation information and actuatable by an observing person, the circuit setting a surgical microscope operating state matched to the device for acquiring endoscopic images in the surgical region when the actuation information for the surgical microscope is present.

By way of example, the circuit can be arranged wholly or partly in the device for acquiring endoscopic images in the surgical region.

A surgical microscope operating state matched to the device for acquiring endoscopic images in the surgical region can consist of, for example, a specific setting of a system for setting the magnification of the observation image of the surgical microscope (magnification system), a specific setting of an illumination system which provides illumination light for illuminating the object region of the surgical microscope, or of a specific setting of filters in an illumination beam path and/or in an observation beam path of the surgical microscope, or else of a specific configuration of a display of the surgical microscope.

Here, the circuit can be an activation circuit which brings the device for acquiring the endoscopic images from a rest state into an activation state and which contains an activation sensor.

Here, a concept of the invention is to embody the activation sensor as a sensor from the group containing gyro sensor, Hall sensor, touch sensor or speech sensor.

According to the invention, it is proposed that the device for acquiring endoscopic images in the surgical region has at least one endoscope. In this case, the activation sensor is preferably arranged in an endoscope body of the endoscope. However, it is noted that the activation sensor can also be arranged in the surgical microscope itself.

A concept of the invention is that the device for acquiring endoscopic images in the surgical region contains at least one endoscope, which, in a first operating state, enables the examination of white light scattered in the surgical region and which, in a further endoscope operating state differing from the first operating state, enables the examination of fluorescence light in a defined wavelength range of a dye, such as 5-ALA, sodium fluorescein (NaFl) or else indocyanine green (ICG), excited to fluoresce in the surgical region and/or the examination of autofluorescence light in the defined wavelength range of biological tissue and/or objects in the surgical region.

The dye 5-ALA is excited to fluoresce with, for example, light with a wavelength of 400 nm$\leq\lambda\leq$410 nm. Then, 620 nm$\leq\lambda\leq$710 nm applies for the wavelength $\lambda$ of the fluorescence light. The dye NaFl is excited to fluoresce with light with a wavelength of 460 nm$\leq\lambda\leq$500 nm. In the process, fluorescence light in the wavelength range of 540 nm$\leq\lambda\leq$690 nm is generated. In order to excite the dye ICG to fluoresce, the latter must be impinged by light with a wavelength of 700 nm$\leq\lambda\leq$780 nm. The wavelength $\lambda$ of the emitted fluorescence light then lies in the wavelength range of 820 nm$\leq\lambda\leq$900 nm.

It is also a concept of the invention that the surgical microscope, in a first surgical microscope operating state, enables the examination of white light scattered in the surgical region and, in a further surgical microscope operating state differing from the first operating state, enables the examination of fluorescence light in a defined wavelength range of a first dye, for example, 5-ALA, excited to fluoresce in the surgical region and/or the examination of autofluorescence in the defined wavelength range of biological tissue and/or objects in the surgical region. Here, the endoscope is configured in such a way that, in a first endoscope operating state, the examination of white light scattered in the surgical region and, in a further endoscope operating state differing from the first operating state, the examination of fluorescence light in the defined wavelength range of the first dye, for example, 5-ALA, excited to fluoresce in the surgical region and/or the examination of autofluorescence light in the defined wavelength range of biological tissue and/or objects in the surgical region is possible. The further endoscope operating state and the further surgical microscope operating state are therefore matched to one another. Here, the surgical microscope and the endoscope are preferably operably coupled to one another in such a way that the further surgical microscope operating state is set automatically, that is, triggered by setting the further endoscope operating state, when the further endoscope operating state is set.

It is moreover a concept of the invention to provide in the visualization system a device for automatically operably coupling the surgical microscope and the first endoscope when the endoscope is activated and/or when the endoscope is picked up by the observing person and/or when a portion of the endoscope is arranged in an observation region of the surgical microscope and/or when fluorescence light and/or autofluorescence light in the defined wavelength range occurs.

According to the invention, it is also proposed that there is a further endoscope in the visualization system, which further endoscope, in at least one endoscope operating state, enables the examination of fluorescence light in a defined further wavelength range of a further dye, for example, NaFl, excited to fluoresce in the surgical region and/or the examination of autofluorescence light in the defined further wavelength range of biological tissue and/or objects in the surgical region, wherein the surgical microscope, in a further surgical microscope operating state differing from the first operating state, enables the examination of fluorescence light in the defined wavelength range of the further dye, for example, NaFl, excited to fluoresce in the surgical region and/or the examination of autofluorescence in the defined wavelength range of biological tissue and/or objects in the surgical region, and wherein the surgical microscope and the endoscope are operably coupleable in such a way that, when the endoscope is operated in this further endoscope operating state, the further surgical microscope operating state is set automatically. Here, a concept of the invention is, in particular, that the device for automatically operably coupling the surgical microscope and the further endoscope is effected automatically, that is, triggered by receiving the further endoscope and/or arranging a portion of the further endoscope in the observation region and/or by the occurrence of fluorescence light and/or autofluorescence light, when the further endoscope is activated and/or when the further endoscope is picked up by the observing person and/or when a portion of the further endoscope is arranged in an observation region of the surgical microscope and/or when fluorescence light and/or autofluorescence light in the defined wavelength range occurs.

In particular, provision can also be made of a further endoscope in the visualization system, which further endoscope, in at least one endoscope operating state, enables the examination of fluorescence light in a defined further wavelength range of a further dye, for example, ICG, excited to fluoresce in the surgical region and/or the examination of autofluorescence light in the defined further wavelength range of biological tissue and/or objects in the surgical region, wherein the surgical microscope, in a further surgical microscope operating state differing from the first operating state, enables the examination of fluorescence light in the defined further wavelength range of the further dye, for example, ICG, excited to fluoresce in the surgical region and/or the examination of autofluorescence in the defined wavelength range of biological tissue and/or objects in the surgical region, and wherein the surgical microscope and the endoscope are operably coupleable in such a way that, when the endoscope is operated in this endoscope operating state, the further surgical microscope operating state is set automatically.

Here, in turn, a concept of the invention is the automatic operable coupling of the surgical microscope and the further endoscope when the further endoscope is activated and/or when the further endoscope is picked up by the observing person and/or when a portion of the further endoscope is arranged in an observation region of the surgical microscope and/or when fluorescence light and/or autofluorescence light in the defined further wavelength range occurs.

In the visualization system according to the invention, the at least one endoscope can be embodied, in particular, as a video endoscope.

Moreover, it is proposed that the visualization system also has a device for rotating an endoscopic image of the surgical region displayed at the display relative to the display.

In a method according to the invention for operating a visualization system, which contains a surgical microscope for observing an operation system with magnification and which has a device for acquiring endoscopic image data in the surgical region, which is operably coupled to the surgical microscope for displaying the endoscopic image data, at least one operating parameter of the surgical microscope is modified when adjusting at least one operating parameter of the video endoscope and/or at least one operating parameter of the video endoscope is varied when adjusting at least one operating parameter of the surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
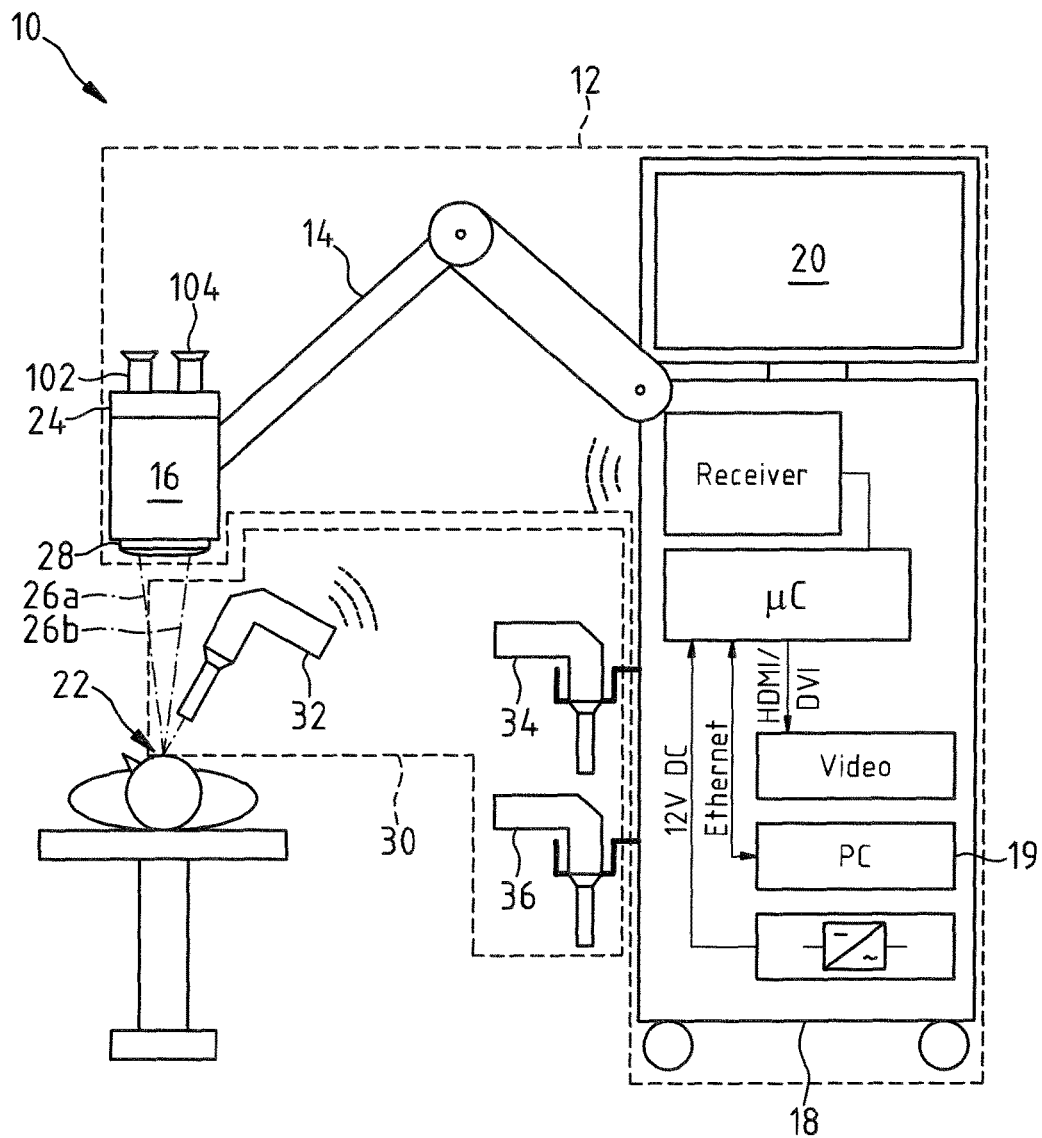
FIG. 1 shows a first visualization system with a surgical microscope and with a device for acquiring endoscopic image data with a first, second and third video endoscope.

The visualization system 10 shown in FIG. 1 is a surgical visualization system. It includes a surgical microscope 12 with a microscope unit 16 accommodated on a stand 14 and with a console terminal 18, which contains a computer unit 19 with a touch-sensitive display 20. The surgical microscope 12 enables for a viewing person the stereoscopic observation of a surgical region 22 in a binocular viewing unit 24. The viewing unit 24 has eyepieces (102, 104) with left-hand and right-hand optical observation beam paths (26a, 26b), which pass through a common microscope main objective 28.

In the visualization system 10 there is a device 30 for acquiring endoscopic image data. The device 30 contains a first, second and third video endoscope (32, 34, 36). The video endoscope 32 allows the examination of the surgical region 22 by acquiring white light scattered in the surgical region 22 and the fluorescence light of the dye 5-ALA excited to fluoresce in the surgical region 22.

The video endoscope 34 serves the examination of the surgical region 22 by acquiring white light scattered in the surgical region 22 and the fluorescence light of the dye sodium fluorescein (NaFl) excited to fluoresce.

The video endoscope 36 is suitable for examining the surgical region 22 by acquiring white light scattered in the surgical region 22 and the fluorescence light of the dye indocyanine green (ICG) excited to fluoresce in the surgical region 22.

The touch-sensitive display 20 of the surgical microscope 12 renders possible, firstly, the control and adjustment of optical imaging parameters of the microscope unit 16 and of the video endoscopes 32, 34, and 36 and, secondly, the separate or simultaneous visualization of the object region 22 observed by means of a video endoscope (32, 34, 36) or by means of the microscope unit 16.

Figure 2:
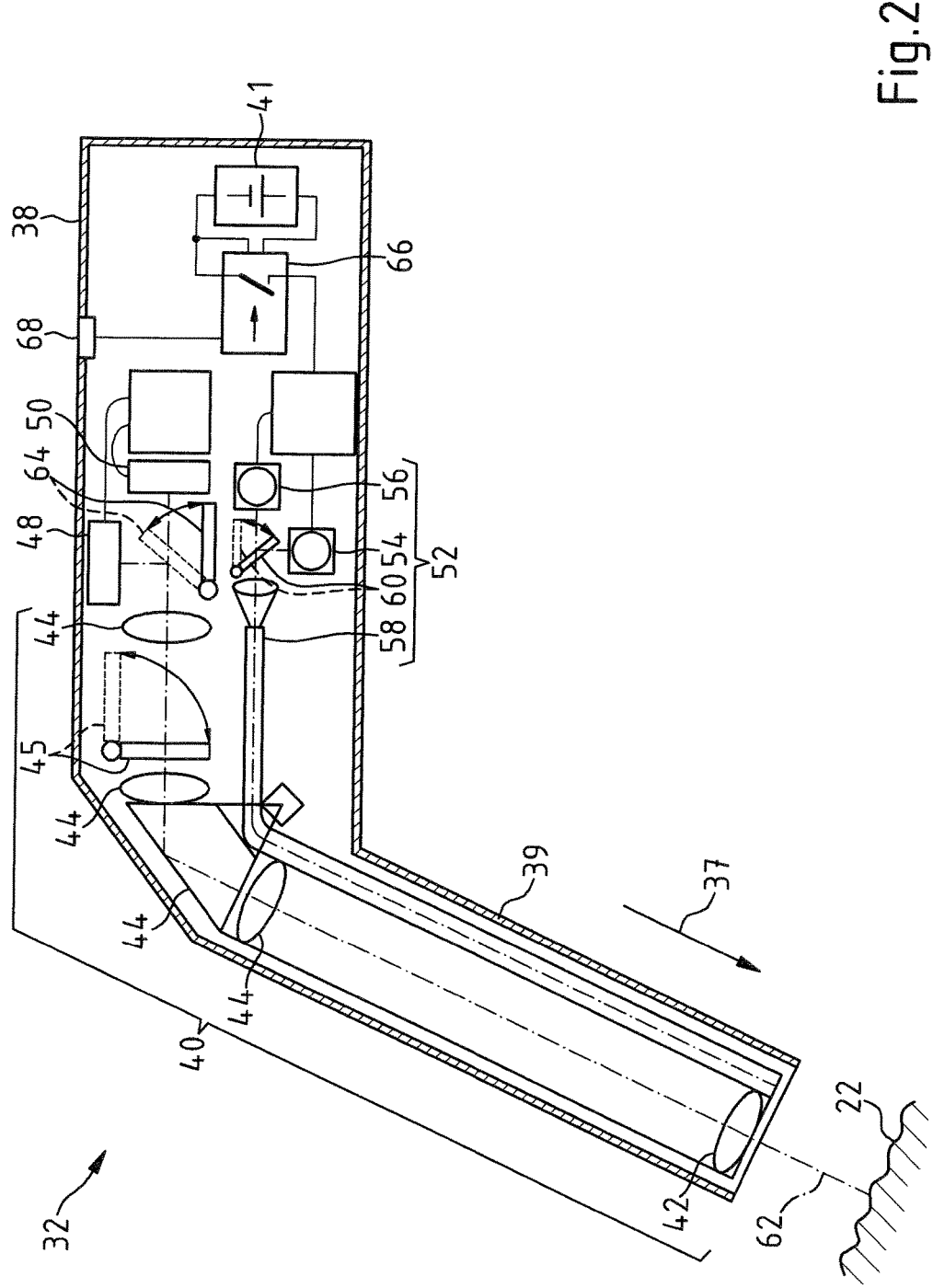
FIG. 2 is a section view through the first video endoscope in the device for acquiring electronic image data.

FIG. 2 shows the configuration of the first video endoscope 32 from FIG. 1. The video endoscope 32 has an endoscope body 39, extended in the longitudinal direction 37, with a handle 38 connected thereto, with an electrical energy store 41 being arranged in the handle. The electrical store 41 is a battery. However, in principle, it also is possible to provide a high performance capacitor as an electrical energy store 41. The video endoscope 32 enables the observation of the object region 46 in a white-light operating mode and in a fluorescence-light operating mode. To this end, the video endoscope 32 contains viewing optics 40 which has an objective assembly 42 and includes an optical transfer system 44 with a folding mirror 45 so as to selectively feed an image of a surgical region 22 to an image sensor 48 sensitive to infrared light and to an image sensor 50 sensitive to light in the visible spectral range.

In order to illuminate the surgical region 22, there is, in the video endoscope 32, an illumination system 52 with a white-light LED 54 and with a light source 56 providing a light with which the fluorescent dye can be excited to fluoresce in a narrow bandwidth. To this end, the illumination system 52 contains an optical waveguide 58 and it has a switchable folding mirror 60, which renders it possible to illuminate the object region 46 selectively with the light from the white-light LED 54 or the light from the light source 56. In order to be able to suppress the fluorescence light emanating from fluorescent objects, for example, the dye ICG, which is scattered in the surgical region 22 and which reaches the transfer system 44 by way of the objective assembly 42, there is a switchable emission filter 64 in the video endoscope 32. The emission filter 64 can selectively be moved into, and out of, the optical imaging beam path 62.

The video endoscope 32 contains an activation circuit 66, which is arranged in the endoscope body 39. The activation circuit 66 has a touch sensor 68 integrated into the handle 38 as an activation sensor, by means of which it is possible to detect the video endoscope 32 being picked up by the hand of an observing person at the handle 38 in order then to bring the video endoscope 32 into a work mode from a rest mode. In this case, the activation circuit 66 effects automatic operable coupling of the video endoscope 32 and the surgical microscope 12. The video endoscope 32 is registered at the computer unit 19 of the surgical microscope 12 by means of the activation circuit 66. It then transmits to the computer unit 19 in a wireless fashion electronic image data which can be displayed at the touch-sensitive display 20 of the surgical microscope 12.

If an observing person releases the handle 38 from the hand, this is detected by means of the touch sensor 68. The activation circuit 66 then brings the video endoscope 32 back into the rest mode. In this way, the electrical energy consumption of the video endoscope 32 can be minimized when the latter is merely provided but not used.

The configuration of the second video endoscope 34 and of the third video endoscope 36 from FIG. 1 corresponds, in principle, to the configuration of the first video endoscope 32. However, in this case, in addition to the white-light LED, the second video endoscope 34 and the third video endoscope 36 each contain a light source and an emission filter which are tuned to the excitation and detection of fluorescence light from the dye 5-ALA or NaFl. Here too, there is an activation circuit with a touch sensor, which has the functionality described above.

Figure 3:
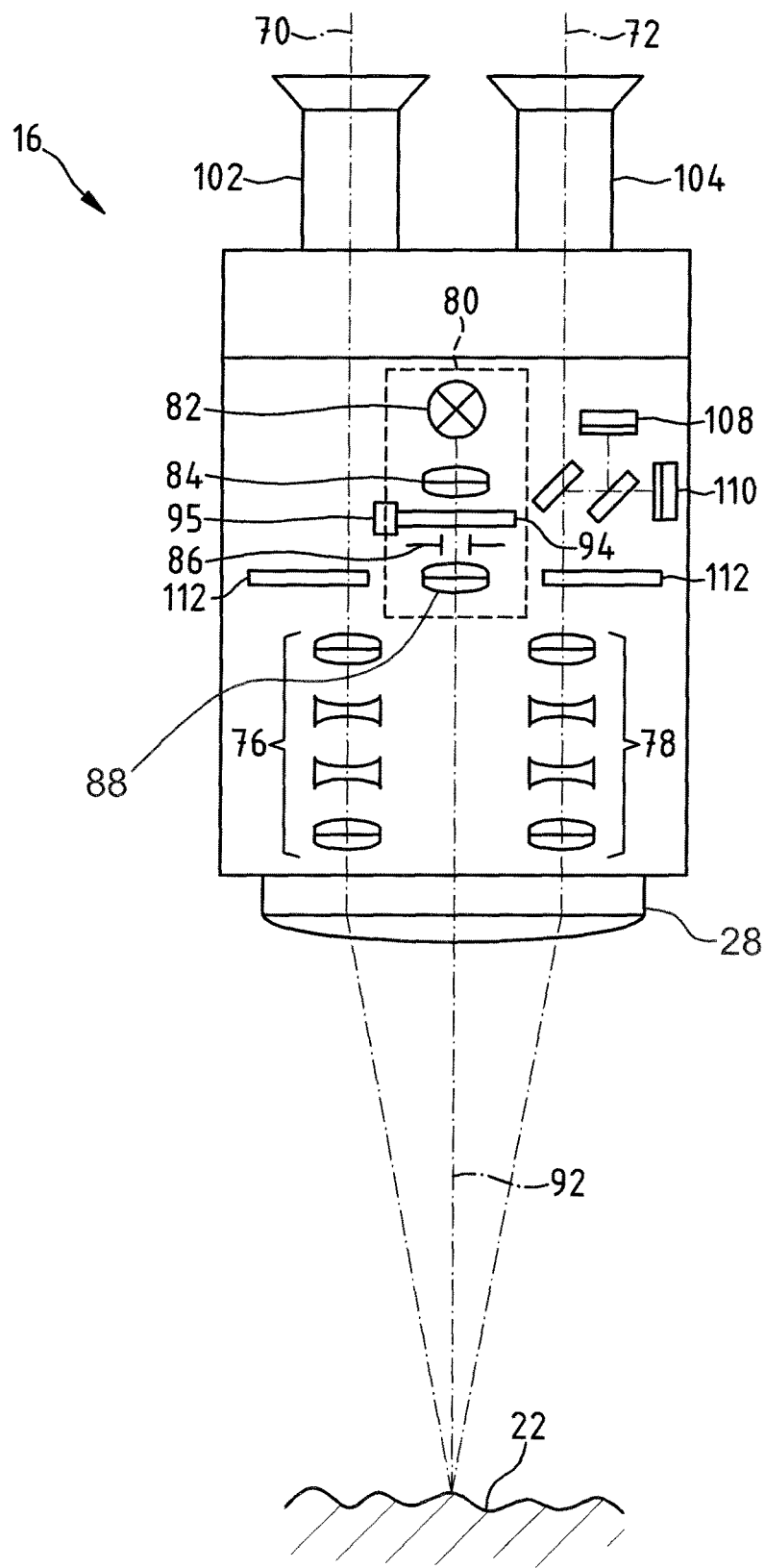
FIG. 3 shows the configuration of the surgical microscope in the surgical visualization system.

FIG. 3 explains the configuration of the microscope unit 16 of the surgical microscope 12 in the visualization system 10. The microscope unit 16 enables a stereoscopic observation of the surgical region 22 with viewing beam paths (70, 72) which pass through a microscope main objective 74. A zoom system (76, 78) is provided in the microscope unit 16 for setting the magnification in the viewing beam paths (70, 72). There is an illumination system 80 with a light source 82 in the microscope unit 16 for illuminating the surgical region 22 with illumination light.

The light emitted by the light source 82 is collimated by collimation optics 84 in the plane of an illumination field diaphragm 86 and guided into the surgical region 22 via the condenser lens 88 and the microscope main objective 28 by way of the illumination beam path 92. The illumination system 80 contains an adjustable filter wheel 94, which is adjustable by means of a drive 95 and which has different filters for setting the spectral composition of the illumination light guided to the surgical region 22.

Figure 4:
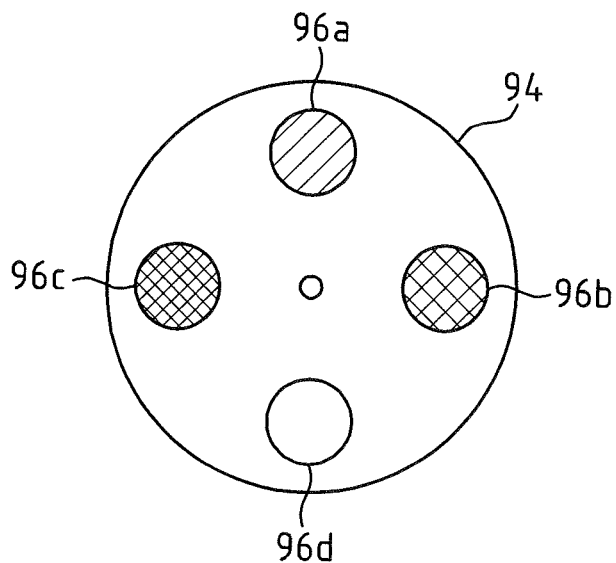
FIG. 4 shows a filter wheel of an illumination system in the surgical microscope.

FIG. 4 shows a plan view of the filter wheel 94. The filter wheel 94 has a pinhole diaphragm 96d and illumination filter (96a, 96b, 96c), by means of which it is possible to set the spectral composition of the illumination light in such a way that the dye ICG or 5-ALA or NaFl can be excited therewith to fluoresce and the light with a wavelength corresponding to the wavelength of the fluorescence light of these dyes being filtered in the process.

Figure 5:
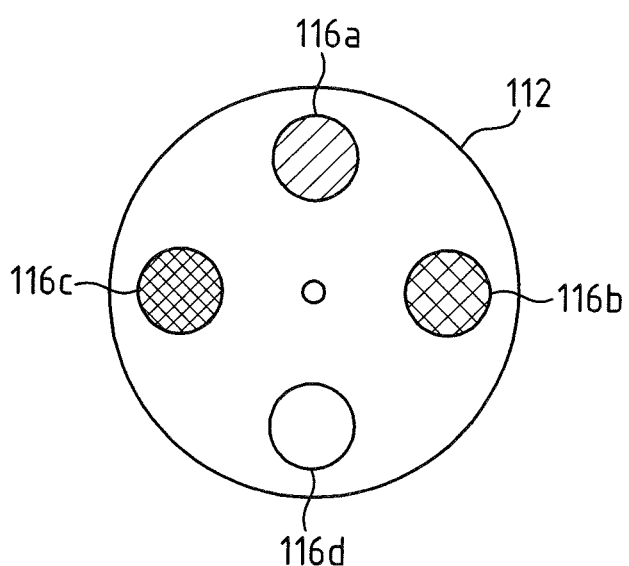
FIG. 5 shows a filter wheel arranged in an observation beam path of the surgical microscope.

There is in each case one adjustable filter wheel 112 in the left-hand and right-hand viewing beam path (70, 72) of the microscope unit 16. FIG. 5 shows a plan view of the filter wheel 112. The filter wheel 112 contains the filters (116a, 116b, 116c) and a pinhole diaphragm 116d. The transmission characteristic of the filters (116a, 116b, 116c) is matched to the transmission characteristic of the illumination filters (96a, 96b, 96c). The filters (116a, 116b, 116c) are used to suppress the light exciting the fluorescence of the dye ICG or 5-ALA or NaFl and pass the light with a wavelength of the fluorescence light of these dyes.

In order to visualize in the surgical region 22 by means of fluorescence light tissue structures in which the dye 5-ALA has accumulated, the filter 96a of the filter wheel 94 is switched into the illumination beam path 92 and the filter 116a of the filter wheel 112 is arranged in the left-hand and right-hand viewing beam path (70, 72). Accordingly, in order to visualize tissue structures in the surgical region 22 in which the dye ICG has accumulated, the filter 96b is arranged in the illumination beam path 92 and the filter 116b of the corresponding filter wheel 112 is positioned in the left-hand and right-hand viewing beam path (70, 72). In order to visualize tissue structures containing the dye NaFl, the filter 96c is switched into the illumination beam path 92 and the filter 116c of the filter wheel 112 is positioned in the left-hand and right-hand viewing beam path (70, 72).

In the microscope unit 16 there is a camera 108 for acquiring IR light and a camera 110, by means of which fluorescence light in the visual spectral range can be detected. The camera 108 and the camera 110 are connected to the computer unit 19 of the surgical microscope 12 shown in FIG. 1.

Figure 6A:
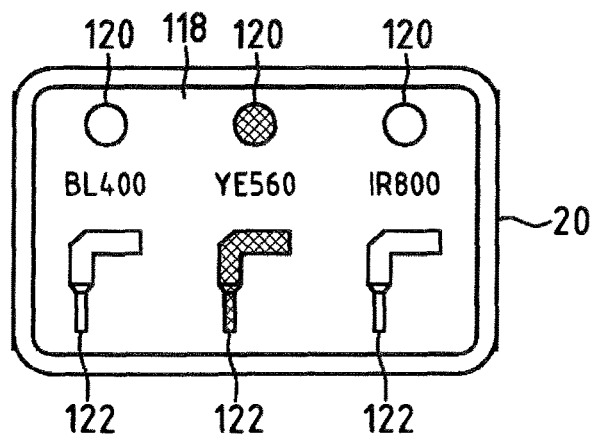
FIG. 6A and FIG. 6B, as well as FIG. 6C and FIG. 6D, show different displays at a display of the surgical microscope.

FIG. 6A shows a display 118 of the display 20 triggered by activating a video endoscope (32, 34, 36). This informs an observing person about which one of the video endoscopes is currently used to conduct work.

Figure 6B:
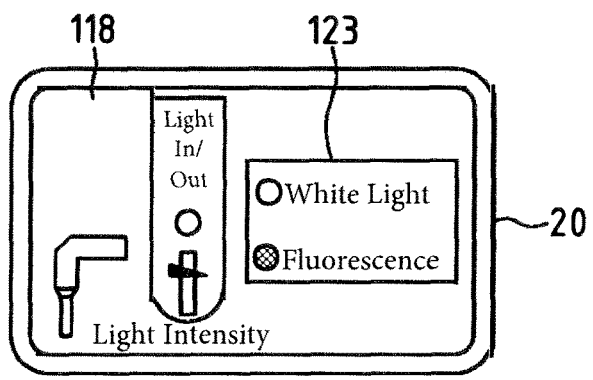

FIG. 6B shows a display 118 of the display 20 with control buttons for controlling an activated video endoscope (32, 34, 36). The control button 123 allows an operator in the correspondingly activated video endoscope (32, 34, 36) to switch between the operating mode for observing the surgical region 22 by means of white light and the operating mode for viewing the surgical region 22 by capturing fluorescence light. Here, the operating mode of the microscope unit 16 is also switched from a white-light operating mode to the fluorescence-light operating mode, and vice versa, when a video endoscope (32, 34, 36) is switched between the white-light operating mode and the fluorescence-light operating mode by means of the corresponding activation circuit. This measure causes the operating state of the surgical microscope 12 to always automatically be matched to the operating state of the employed video endoscope (32, 34, 36) in the visualization system 10.

Figure 6C:
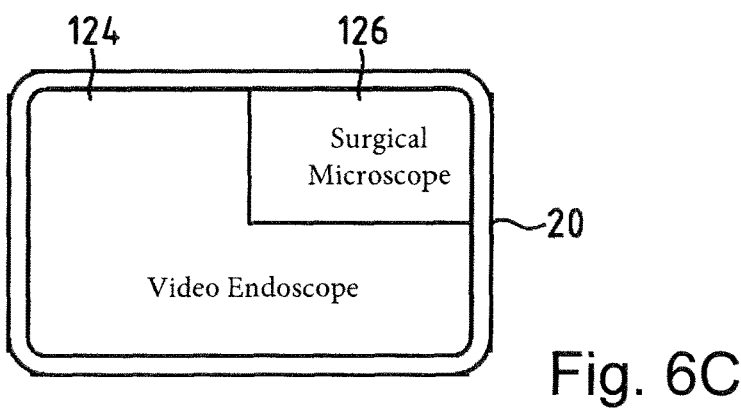
FIG. 6E shows a full screen observation image of the video endoscope; and, FIG. 7 shows a further visualization system with an surgical microscope and with a device for acquiring endoscopic image data with a first, second and third video endoscope.
Figure 6D:
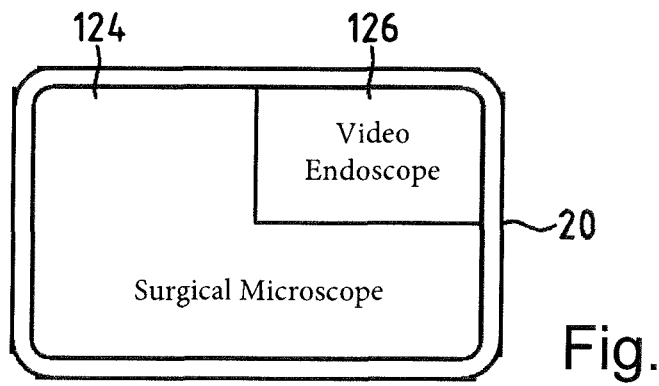

FIG. 6C and FIG. 6D each show an observation image from a video endoscope (32, 34, 36) and an observation image from the microscope unit 16 at the display 20. Here, the observation image from the video endoscope (32, 34, 36) and from the microscope unit 16 is visualized in two mutually separated fields (124, 126), which have different dimensions. By touching the corresponding smaller field 126, an observing person in this case can selectively cause the observation image from the microscope unit 16 or from the selected video endoscope (32, 34, 36) to be displayed in the larger field 124.

Optionally, provision can also be made in the visualization system for the observation image of a corresponding video endoscope (32, 34, 36) to be brought automatically to the display in the larger field 124, triggered by picking up or switching on the specific video endoscope (32, 34, 36) by an observing person. That is, in this case, the activation sensor 68 for a video endoscope (32, 34, 36) is integrated into the surgical microscope 12 and the activation circuit 66 is situated partly in the surgical microscope 12 and partly in a video endoscope (32, 34, 36) in each case.

Figure 6E:
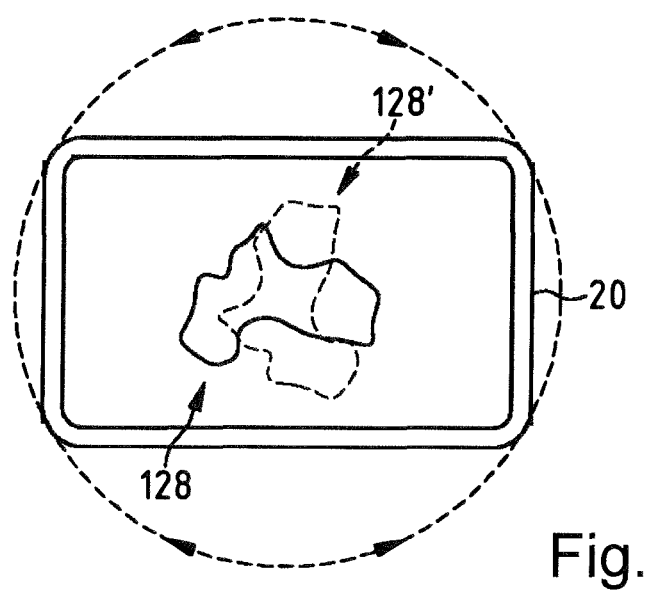

FIG. 6E shows a full screen 128 observation image of the video endoscope (32, 34, 36). An observing person can rotate this full screen 128 by virtue of wiping the fingers of a hand over the display 20 in a manner following a direction of rotation or by virtue of touching a desired rotational position of the image (128, 128') with the fingers of a hand at the display 20.

It should be noted that, in an alternative embodiment of the surgical visualization sensor, a video endoscope (32, 34, 36) may also have a gyro sensor instead of a touch sensor as an activation sensor in the activation circuit 66, which gyro sensor switches the corresponding video endoscope (32, 34, 36) into a work state when detecting a displacement thereof. As an alternative thereto, it is also possible to provide a Hall sensor in the activation circuit, by means of which it is possible to detect whether the corresponding video endoscope (32, 34, 36) is moved out of a rest position in which the video endoscope (32, 34, 36), in the portion of the Hall sensor, is exposed to a defined magnetic field. Moreover, it should be noted that, in order to switch a video endoscope from a rest state into a work state, provision can also be made in the activation circuit 66 for a speech sensor as activation sensor instead of the aforementioned sensors.

Figure 7:
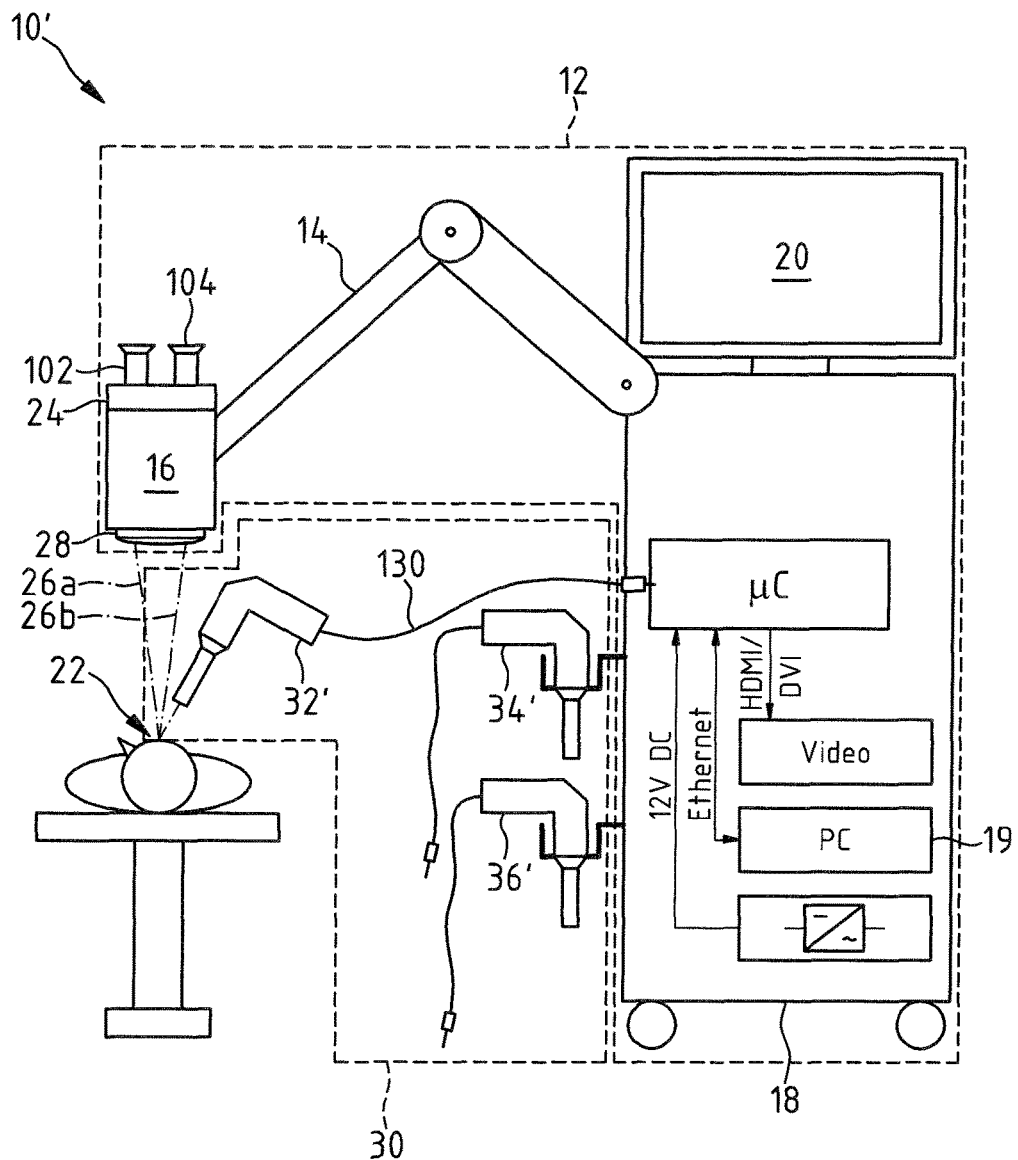

FIG. 7 shows a further visualisation system 10' with a surgical microscope 12 and with a device for acquiring electronic image data with a first, a second and a third video endoscope (32', 34', 35'). To the extent that the assemblies of the visualization system 10' and elements in FIG. 7 correspond to elements and assemblies from the preceding figures, these are identified by the same numbers as reference signs. In order to connect the video endoscopes (32', 34', 36') to the surgical microscope 12, provision is made here for a cable 130 with a plug 132 and a socket 134 formed in the console terminal 18 of the surgical microscope 12. Plugging the plug 132 into the socket 134 in this case actuates an activation circuit arranged in the corresponding video endoscope (32', 34', 36'), which activation circuit, when activated, causes the corresponding video endoscope (32', 34', 36') to be registered by the computer unit 19 of the surgical microscope 12 and sets a work operating mode for the corresponding video endoscope (32', 34', 36'). A consequence of this measure then is the display of the operating parameters of the corresponding video endoscope (32', 34', 36') at the display 20 and it therefore enables a display of the observation image thereof. Conversely, if the plug-in connection between video endoscope (32', 34', 36') and surgical microscope 12 is opened, the consequence thereof is a deregistration of the corresponding video endoscope (32', 34', 36') at the surgical microscope 12 and the corresponding video endoscope is put into a rest mode.

In conclusion, the following, in particular, should be registered: The invention relates to a visualization system (10, 10') with a surgical microscope 12 for observing a surgical region 22 with magnification, having a computer unit 19 with a display 20 for displaying image data. The visualization system (10, 10') comprises a device 30 for acquiring endoscopic image data in the surgical region 22, which is operably coupled to the surgical microscope 12 for displaying the endoscopic image data. The device 30 for acquiring endoscopic image data in the surgical region 22 contains a circuit 66 which is configured for acquiring actuation information and actuatable by an observing person, the circuit setting a surgical microscope operating state matched to the device 30 for acquiring endoscopic images in the surgical region 22 when the actuation information for the surgical microscope 12 is present.

It is understood that the foregoing description is that of the preferred embodiments of the invention and that various changes and modifications may be made thereto without departing from the spirit and scope of the invention as defined in the appended claims.

LIST OF REFERENCE SIGNS 10, 10' Visualization system
12 Surgical microscope
14 Stand
16 Microscope unit
18 Console terminal
19 Computer unit
20 Display
22 Surgical region
24 Binocular viewing unit
26a, 26b Observation beam path
28 Microscope main objective
30 Device for acquiring endoscopic image data
32, 32', 32", 34, 34', 36, 36' Video endoscope
37 Longitudinal direction
38 Handle
39 Endoscope body
40 Viewing optics
41 Electrical energy store
42 Objective assembly
44 Optical transfer system
45 Folding mirror
46 Object region
48, 50 Image sensor
52 Illumination system
54 White-light LED
56 Light source
58 Optical waveguide
60 Folding mirror
62 Imaging beam path
64 Emission filter
66 Activation circuit
68 Touch sensor
70, 72 Viewing beam path
74 Microscope main objective
76, 78 Zoom system
80 Illumination system
82 Light source
84 Collimation optics
86 Illumination field diaphragm
88 Condenser lens
92 Illumination beam path
94 Filter wheel
95 Drive
96a, 96b, 96c Filter
96d Pinhole diaphragm
102, 104 Eyepiece
108, 110 Camera
112 Filter wheel
116a, 116b, 116c Filter
116d Pinhole diaphragm
118 Display
123 Control button
124, 126 Field
128, 128' Image
130 Cable
132 Plug
134 Socket

What is claimed is:
1. A visualization system comprising:
a surgical microscope assembly for viewing a surgical region under magnification;
said surgical microscope assembly including a computer unit having a display for displaying image data;
a detection arrangement which includes an endoscope to detect endoscopic images in the surgical region and being operatively coupled to said surgical microscope assembly;
a circuit actuable by a viewing person and said circuit being configured to detect actuation data;
said circuit being configured to set an operating state of said surgical microscope assembly matched to said detection arrangement in response to a presence of said actuation data for said surgical microscope assembly;
said surgical microscope assembly having a first operating state wherein white light is scattered in the surgical region and permits viewing said surgical region in a white light operating mode; and, a second operating state, different from said first operating state, wherein:
(a) fluorescence light permits viewing said surgical region in a fluorescence light operating mode in a defined wavelength range of a first dye (5-ALA), which is excited to fluorescence in the surgical region, and/or
(b) autofluorescence light permits viewing said surgical region in an autofluorescence light operating mode in the defined wavelength range of biological tissue and/or objects in the surgical region;
said endoscope having a first operating state wherein said endoscope permits examination in a white light operating mode and a second operating state wherein said endoscope permits examination in fluorescence light in the defined wavelength range of the first dye (5-ALA, NaFl, ICG) in the surgical region, the dye being excited to fluorescence, and/or the examination in autofluorescence light in the defined wavelength range of biological tissue in the surgical region;
said first and second operating states of said surgical microscope assembly being matched to corresponding ones of said first and second operating states of said endoscope; and,
said surgical microscope assembly and said endoscope being operatively coupled so as to cause the operating state of said surgical microscope assembly to be automatically set to the operating state of said endoscope corresponding thereto.

2. The visualization system of claim 1, wherein said circuit is an activation switching circuit configured to transfer said detection arrangement from a rest state into an activation state; and, said activation switching circuit includes an activation sensor selected from the group including a gyro sensor, Hall sensor or voice sensor.

3. The visualization system of claim 2, wherein said endoscope has an endoscope body wherein said activation sensor is mounted.

4. The visualization system of claim 2, wherein said activation sensor is mounted in said surgical microscope.

5. The visualization system of claim 1, wherein said visualization system further comprises a coupling unit for automatically operatively coupling said surgical microscope assembly and said endoscope when said endoscope is activated and/or when said endoscope is taken up by an operator and/or when there is a command of a section of said endoscope in a viewing region of said surgical microscope assembly and/or when there is an occurrence of fluorescence light and/or autofluorescence light in the defined wavelength range.

6. The visualization system of claim 5, wherein said endoscope is a first endoscope; and, wherein said detection arrangement comprises a second endoscope which, in a second endoscopic operating state, permits the examination of fluorescence light in a defined further wavelength range of a further dye (NaFl), which is excited to fluorescence, in the surgical region and/or which permits the examination in autofluorescence light in the defined further wavelength range of biological tissue in the surgical region; said operating state of said surgical microscope assembly is a first operating state; said surgical microscope assembly has a second operating state different from said first operating state thereof which permits the examination of fluorescence light in the defined further wavelength range of an additional dye (NaFl), which is excited to fluorescence, in the surgical region, and/or the examination of an autofluorescence light in the defined further wavelength range of biological tissue and/or objects in the surgery region; and, wherein the surgical microscope assembly and said second endoscope are operatively couplable so that the second operating state of the surgical microscope assembly is automatically terminated when there is an operation of the second endoscope in the second endoscope operating state.

7. The visualization system of claim 6, wherein said system further comprises a coupling unit for automatically operatively coupling the surgical microscope assembly and the second endoscope when there is an activation of the second endoscope and/or when a viewing person takes up the second endoscope and/or when there is a command of a section of the second endoscope in a viewing region of the surgical microscope assembly and/or when there is an occurrence of fluorescence light and/or autofluorescence light in the defined further wavelength range.

8. The visualization system of claim 7, wherein said detection arrangement includes a third endoscope which permits, in an endoscopic operating state, the examination of fluorescence light in a defined further wavelength range of a further dye (ICG), which is excited to fluorescence, in the surgical region and/or the examination of autofluorescence in the defined further wavelength range of biological tissue and/or objects in the surgical region; wherein the surgical microscope assembly permits, in a second operating state thereof different from the first operating state thereof, the examination of fluorescence light in the defined further wavelength of the dye (ICG), which is excited to fluorescence, in the surgical region and/or the examination of an autofluorescence light in the defined wavelength range of biological tissue and/or objects in the surgical region; and, the surgical microscope assembly and the third endoscope are operatively couplable so that, when operating the third endoscope in this further endoscope operating state, the additional operating state of the surgical microscope assembly is automatically terminated.

9. The visualization system of claim 8, wherein said system further comprises a coupling unit for automatically operatively coupling the surgical microscope assembly and the third endoscope where there is an activation of the third endoscope and/or when taking up the third endoscope by a viewing person and/or when there is a command of a section of the third endoscope in a viewing region of the surgical microscope assembly and/or when there is an occurrence of fluorescence light and/or autofluorescence light in the defined further wavelength range.

10. The visualization system of claim 9, wherein at least one of the endoscopes is configured as a video endoscope.

11. The visualization system of claim 8, wherein said system further comprises a unit configured to rotate an endoscopic image, which is shown on the display and is from the surgical region, relative to the display.

* * * * *